(12) United States Patent
Yoshida

(10) Patent No.: US 8,859,808 B2
(45) Date of Patent: Oct. 14, 2014

(54) METHOD FOR OBTAINING LACTIC ACID WITH A HIGH DEGREE OF PURITY FROM FERMENTATIVE LIQUOR

(76) Inventor: Paulo Yoshida, Rio de Janeiro (BR)

(*) Notice: Subject to any disclaimer, the term of this patent is extended or adjusted under 35 U.S.C. 154(b) by 0 days.

(21) Appl. No.: 13/817,722

(22) PCT Filed: Aug. 17, 2011

(86) PCT No.: PCT/BR2011/000288
§ 371 (c)(1),
(2), (4) Date: Feb. 19, 2013

(87) PCT Pub. No.: WO2012/021956
PCT Pub. Date: Feb. 23, 2012

(65) Prior Publication Data
US 2013/0245320 A1    Sep. 19, 2013

(30) Foreign Application Priority Data
Aug. 19, 2010   (BR) ..................................... 1009166

(51) Int. Cl.
*C07C 51/42*   (2006.01)
*C07C 51/487*   (2006.01)
*B01D 59/50*   (2006.01)

(52) U.S. Cl.
CPC ............... *C07C 51/42* (2013.01); *C07C 51/487* (2013.01); *B01D 59/50* (2013.01)
USPC ........................................................ 562/580

(58) Field of Classification Search
None
See application file for complete search history.

(56) References Cited

U.S. PATENT DOCUMENTS

| 4,275,234 | A | 6/1981 | Baniel et al. |
| 5,250,182 | A | 10/1993 | Bento et al. |
| 5,503,750 | A | 4/1996 | Russo, Jr. et al. |
| 6,319,382 | B1 | 11/2001 | Norddahl |
| 6,478,965 | B1 | 11/2002 | Holtzapple et al. |
| 7,144,977 | B2 * | 12/2006 | Eyal et al. ..................... 528/354 |

FOREIGN PATENT DOCUMENTS

| EP | 0375463 A1 | 6/1990 |
| EP | 1094054 A1 | 4/2001 |

OTHER PUBLICATIONS

P. Pal et al.: "Process intensification in lactic acid production: A review of membrane based process," Chemical Eng. and Proc.: Process Intensification, vol. 48, pp. 1549-1559, 2009.

* cited by examiner

*Primary Examiner* — Brandon Fetterolf
*Assistant Examiner* — Ana Z Muresan
(74) *Attorney, Agent, or Firm* — Rothwell, Figg, Ernst & Manbeck, P.C.

(57) ABSTRACT

The present invention describes a process for obtaining lactic acid with a high degree of purity from a fermentative liquor (1) containing sodium lactate, with a view to the production of polylactic acid. The process comprises the unitary operations of centrifugation (101), centrifugal decantation (102), microfiltration (103), ultrafiltration (104), primary filtration in an activated charcoal bed (105), conventional electrodialysis (201), ion exchange columns in a chelating resin bed (202), bipolar electrodialysis (203), ion exchange columns (204), primary evaporation under vacuum (302), secondary filtration in an activated charcoal bed (304), liquid-liquid extraction from the aqueous phase to the organic phase (305), back extraction from the organic phase to the aqueous phase (306), and secondary, atmospheric evaporation (402).

21 Claims, 4 Drawing Sheets

METHOD FOR OBTAINING LACTIC ACID WITH A HIGH DEGREE OF PURITY FROM FERMENTATIVE LIQUOR

CROSS REFERENCE TO RELATED APPLICATIONS

This application is a 35 U.S.C. §371 National Phase Entry Application from PCT/BR2011/000288, filed Aug. 17, 2011, and designating the United States, which claims priority under 35 U.S.C. §119 to Brazilian Patent Application No. PI 1009166-1 filed Aug. 19, 2010, which is incorporated herein in its entirety.

FIELD OF THE INVENTION

The present invention belongs to the field of processes for obtaining lactic acid with high purity degree from a fermentative liquor containing sodium lactate aiming at polylactic acid production.

BACKGROUND OF THE INVENTION

Lactic acid (2-hydroxypropionic acid) has been increasingly used worldwide in the production of several biodegradable polymers motivated by modern applications in the medical field (as, for example, in artificial prosthesis) and in the pharmaceutical area (as, for example, in medicines with controlled release) and by the strong ecological appeal of using biodegradable polymeric materials based on lactic acid (polylactic acid) from plant substrates in place of plastic of mineral origin. The success of the employment of a green route for the production of polylactic acid requires a complex process that ensures the removal of all of the contaminants in a natural raw material, the isolation of lactic acid and the concentration of the same.

Below are listed the main processes presented in the prior art for the solution of problems of regeneration, purification and concentration of lactic acid produced in fermentation media. As the techniques differ significantly depending on the approach adopted in each invention, subsections are adopted depending on the technology used as base of each patent document.

Generally speaking, it is verified that all of these technologies have as focus the isolated solution of problems of regeneration, purification or concentration which, separately, are ineffective in producing high-purity lactic acid from fermentative liquor with fibers, shells and other hardly removable impurities.

Processes of Membrane Permeation

U.S. Pat. No. 4,110,175 patent document refers to a electrodialysis process that uses anionic and cationic membranes with the purpose of removing organic acids including lactic acid, present in fruit juices and other aqueous solutions.

EP 230021 patent document describes a continuous fermentative process coupled to a electrodialysis process for the continuous removal of lactic acid. However, as there are separations and preliminary filtrations, various components of the fermentative liquor are adhered to the surface of polymeric membranes, which implies in a significant increase in the consumption of electrical energy.

Boyaval et al. (*Biotechnology Letters*, vol. 9, n° 5, pp. 207-212, 1987) presented a process composed of three unit operations: lactate production via fermentation, removal of cells and cell fragments through ultrafiltration and concentration/purification of lactic acid by electrodialysis. However, as prefiltration are not made, ultrafiltration membranes permeability is reduced drastically over time, requiring frequent chemical cleaning of ultrafiltration modules.

U.S. Pat. No. 5,002,881 patent document refers to a fermentation process in which the fermentation product undergoes an operation of ultrafiltration where the retained returns to the fermentation dorna and the permeate corresponding to a solution of ammonium lactate is concentrated through a reverse osmosis operation. Concentrated ammonium lactate is then fed to the electrodialysis operation for recovery and purification of lactic acid. During electrodialysis ammonia hydroxide is formed, which can be returned to the fermentation for pH correction. As disadvantage it can be highlighted the fact that the solution of concentrated ammonium lactate has also unconverted sugars, vitamins, proteins and other contaminants, thus contributing to the electrodialysis efficiency decrease and resulting in a thermally unstable product.

U.S. Pat. No. 5,503,750 patent document refers to a process with a membrane separation operation sequence (ultrafiltration, nanofiltration and reverse osmosis) for the concentration of an ammonium lactate solution and subsequent conversion into lactic acid. As a disadvantage of this process one can highlight the low recovery efficiency (of approximately 54%), other than the fact that the conversion of ammonium lactate into lactic acid uses ion exchange resins (which implies in a large amount of resins, and require subsequent regeneration operations).

U.S. Pat. No. 4,882,277 patent document aims to simplify all the steps used for the purification of lactic acid using only three unit operations: microfiltration, ultrafiltration, and electrodialysis, performed continually throughout the fermentation. The focus of this document is in the arrangement of conventional electrodialysis operation on a laboratory scale.

Complementing the previous document, the U.S. Pat. No. 4,885,247 patent document proposes an arrangement closer to the industrial application, highlighting the possibility of return of residual lactate to the fermenter in order to decrease the alkaline solution demand for controlling the acidity of the medium and reduce process losses.

U.S. Pat. No. 6,319,382 patent document refers to a fermentation (using ammonia to pH correction), purification and regeneration process of lactic acid that consists of a fermentation step, followed by microfiltration and ultrafiltration for withdrawal of cells, cell fragments and macromolecules. The permeate passes through ion exchange resins (chelate resin) for the substitution of bivalent cations by monovalent cations (such as sodium), thus avoiding the formation of insoluble salts that could damage the membranes of the subsequent electrodialysis process. The permeated having no bivalent cations then is submitted to an electrodialysis process for the regeneration of conventional acid and then to the bipolar electrodialysis to acid concentration. One may highlight as a disadvantage of this process the fact of having a high consumption of chemicals for the regeneration of ion-exchange columns, the product loss corresponding to the hold-up (retention) of ion exchange columns in each regeneration, and the requirement for a proper monitoring of the contamination of regenerative solutions. Moreover, these operations do not guarantee the withdrawal of organic contaminants that generate color to the product and lead to thermal instability by the formation of Maillard compounds.

US 2004/033573 A1 American patent document refers to a process that uses membrane separation steps including ultrafiltration, nanofiltration, reverse osmosis and electrodialysis. In this proposal, the fermentative liquor is ultraconcentrated for the retention of high molecular weight substances. Acidification of the permeated is then made to a pH below 3.9. The acidified solution undergoes a step of isolation via nanofiltration and/or reverse osmosis, which promotes the retention of bivalent ions, proteins, other nutrients and organic anions (such as the lactate anion) and permeates molecules free of charge (such as sodium lactate). Afterwards, it may be considered the use of bipolar electrodialysis for the concentration of the lactic acid solution. The use of nanofiltration and/or reverse osmosis constitutes an alternative to conventional electrodialysis process.

Ion Exchange Processes

EP 0393818 European patent document complements the U.S. Pat. No. 4,885,247 American patent document, including two steps of ion exchange after the electrodialysis step. Strong acidic ion exchange resins are used for the removal of sodium cations that were not removed during conventional electrodialysis and basic ion exchange resins weak to remove sulfate anions.

U.S. Pat. No. 5,571,657 patent document proposes modification of strong acidic ion exchange resins through contact with ammonium and/or amine solutions, so as to increase their selectivity to the $Na^+$ cation, thereby increasing the efficiency of the lactic acid regeneration process of sodium lactate solutions.

Extractive Processes

U.S. Pat. No. 4,275,234 patent document presents a recovery process of organic acids aqueous solution using an initial organic solvent extraction followed by a second heated water extraction. It is worth noting that this application is restricted to solutions wherein the organic acid is in its free form.

BR8906651 Brazilian patent document proposes a process for purification and recovery of lactic acid from the solutions containing the same, through a sequence of liquid-liquid extractions. Initially, an aqueous solution of lactate and lactic acid is added with a complex forming agent (composed of at least one octol macolytic) generating octol-lactic acid. Afterwards, this aqueous phase passes through a liquid-liquid extraction with an organic solution of saturated halogenated cyclo-alkanes, alkylated and/or halogenated aromatic hydrocarbons and petroleum ether. The organic phase is separated and then passes through a liquid-liquid extraction with water or methanol. As disadvantages, one can highlight the high reaction time for the complex formation (about 8 h), the need of expensive complexing agents and risks associated with the use of aromatic organic solvents that imply a series of operational difficulties.

Works such as those of B. Bar and J. L. Geiner (*Biotechnology Progress*, vol. 3, n. 109, 1987), Malmary et al (*J. Chem. Technol. Biotechnol.*, n. 75, pp. 1169-1173, 2000), Hartl and Marr (*Separation Science and Technology*, n. 28, pp. 805-819, 1993) and San-Marin and Cheryan (*J. Chem. Technol. Biotechnol.*, n. 65, pp. 281-285, 1996) attested the separation efficiency of lactic acid extraction in an aqueous solution by means of long-stream trialkylamines and low basicity, which are able to form complexes with carboxylic acids for even low concentrations of solute, keeping a high selectivity.

U.S. Pat. No. 4,444,881 patent document presents a process capable of purifying organic acids of a diluted solution from fermentation. This solution is treated with a tertiary amine carbonate (for example, tributylamine or tricyclohexylmethylamine), resulting in a precipitate of calcium carbonate and organic salt of trialkylammonium. Organic salt solution is isolated, concentrated by extraction with solvent, distilled and heated for the generation of lactic acid and tertiary amine. As a disadvantage it may be highlighted the cost of specific chemical products, such as tertiary amines, and the absence of organic acids post-treatments to ensure the absence of impurities.

U.S. Pat. No. 4,771,001 patent document presents a process for continuous removal of lactate during fermentative liquor of cheese whey. During fermentation the separation and recycling of cells is made via microfiltration and ultrafiltration, wherein the permeate follows the purification steps. The permeate is acidified and then passes through a liquid-liquid extraction with a solution (immiscible in water) of a tertiary trialkylamine of 24 carbons, and an organic solvent. The organic phase is then separated and passes through a liquid-liquid extraction using a suspension of alkali solids and alkali-earth solids in an aqueous solution of ammonium hydroxide, which promote the removal of lactate and lactic acid. In this patent document concentration steps are not addressed or even lactic acid isolation.

U.S. Pat. No. 5,510,526 patent document uses as extracting phase a trialkylamine solution with a strong attraction to lactic acid (for example, tri-n-octylamine and tri-n-dodecylamine) in an extraction with atmosphere of $CO_2$. Sodium bicarbonate crystals are formed and separated from the aqueous phase. Bicarbonate is converted to carbonate and returns to the fermentation process being used for pH neutralization. The alkylamine type used should be chosen so that its power of attraction is high enough to extract the lactic acid from lactate solution and weak enough to deliver the acid to the water. Because they are viscous, these alkylamines should be added from kerosene and/or octanol. The removal of lactic acid from the organic phase is done through contact with water. In the case of kerosene or octanol being used, a step prior to rinsing with water must be made to remove these solvents.

U.S. Pat. No. 6,478,965 patent document presents a route in the use of secondary or tertiary amines (e.g., TEA, or DEMA) in the extraction of water from a stream diluted in lactic acid (about 3%), thus producing a concentrated stream of 15% lactic acid. It is necessary a series of contactors to promote the extraction of water from the organic phase.

U.S. Pat. No. 6,509,179 patent document combines a set of unit operations for purification of lactic acid formed by the steps of acidification, salt removal, activated carbon filtration, primary extraction, secondary extraction, evaporation and vacuum distillation.

U.S. Pat. No. 7,026,145 patent document proposes an improvement in the process of lactic acid extraction using tertiary alkylamines using sulfuric acid along with the amine solution, as well as a preliminary acidification step using this same acid.

US 2004/210088 A1 American document describes several routes of lactic acid production based on liquid-liquid extraction with amines and/or and specific alcohols, the removal of the solvent being made by distillation columns in the top product or in the bottom product (depending on the route considered).

U.S. Pat. No. 7,019,170 patent document describes the recovery of lactic acid from a lactic acid solution and lactate through a sequence of liquid-liquid extraction operations. A first liquid-liquid extraction column promotes the exchange of mass between a stream of lactic acid and lactate and a stream of trialkylamine, generating a stream of primary raffinate and a saturated trialkylamine stream. The saturated trialkylamine stream passes through a column of liquid-liquid extraction with pure water, generating a stream of pure lactic acid and a stream of trialkylamine "alive". A third column of liquid-liquid extraction promotes contact between the primary and raffinate trialkylamine stream "alive", generating a stream of secondary raffinate and a stream of trialkylamine recovered (which can be returned to the first extraction operation).

Evaporative Processes

U.S. Pat. No. 6,489,508 patent document details the process of lactic acid concentration by evaporation highlighting the optimum operating conditions of either pressure (vacuum) and temperature, so as to minimize the change of color of the final product.

The international publication WO 00/56693 A1 describes a vacuum distillation process followed by crystallization, which allows the concentration of a solution of 80% lactic acid up to a concentration of 99%. The high energetic consumption of the evaporation and crystallization operations coupling is a significant disadvantage of this proposal.

U.S. Pat. No. 6,384,276 patent document proposes the acidification of a lactic acid and sodium lactate solution. Then, an evaporative crystallization is made, wherein which sodium lactate is crystallized and the lactic acid is kept in solution. It is observed, however, that the success of this proposal depends on having as load a pure solution (free of sugars, proteins, or vitamins), otherwise there will be contamination of the final product and the generation of a product with color.

Alternative Processes

U.S. Pat. No. 5,177,008 patent document proposes the use of chromatographic separation operations for the separation of lactic acid for the reuse of that product from the secondary streams of the ethanol industry. However, the high cost of this process, mainly for production of lactic acid on a large scale, significantly restricts the application of this technology.

CN 101234960 patent document proposes a concentration process which promotes initial evaporation of lactic acid followed by rotating distilling (also called molecular distillation), generating a stream of lactic acid with high purity.

It would be helpful if the technique had a process of obtaining lactic acid from fermentation broths that use clarification, regeneration, purification and liquor concentration, the process operating under energetic efficiency regimen by recycling the process streams, the final product being concentrated lactic acid and having high purity degree.

SUMMARY OF THE INVENTION

In a broad way, in order to produce a lactic acid with high purity degree from fermentative broths keeping a high global yield, it was developed in the present invention a process consisting of a sequence of unit operations and several recycling streams for by-products reuse and intermediate streams.

These operations involve:

a) clarification of the fermentative liquor containing sodium lactate through the centrifugation, microfiltration, and tangential ultrafiltration operations and finishing by filtration over activated carbon, obtaining a clarified sodium lactate solution;

b) regeneration of said solution obtained in the step a) by submission of the same to the conventional electrodialysis (EDC) and bipolar electrodialysis;

c) submission of the solution to ion exchange with resins, thus obtaining a stream with 80 to 200 g/L of lactic acid and 10-20% of sodium lactate;

d) purification of the lactic acid from step c) by evaporation, thus generating a stream of lactic acid containing 1-5% of impurities. The concentrated lactic acid obtained is contacted with activated carbon, thus obtaining colorless concentrated lactic acid, which must be extracted with organic alcohol solution or alcohol-amine and, after extraction, washed with water to eliminate impurities. At the end of the step, lactic acid purified at 5-10 g/L containing 0.01 to 3% of impurities is obtained; and e) lactic acid evaporation purified to obtain concentrated lactic acid 80-90% and purified.

Energetic efficiency is ensured through the thermal energy reuse operations of intermediate streams.

Thus, the invention provides a process for obtaining concentrated lactic acid and of high purity degree through the steps for clarification, regeneration, purification, and concentration, the lactic acid being derived from fermentative liquor containing sodium lactate and multiple contaminants present in the fermentation process substrates.

Additionally, in the process of obtaining concentrated lactic acid and of high purity degree of the present invention, the steps proposed are synergistically combined.

DETAILED DESCRIPTION OF THE INVENTION

Figure 1:
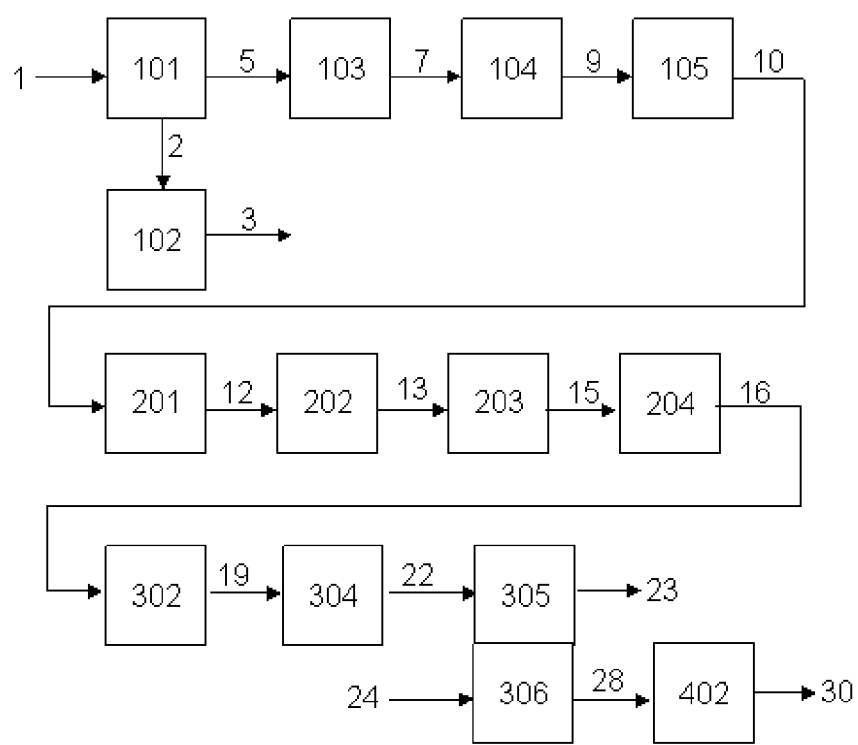
FIG. 1 attached is a block diagram that represents in a simplified way the sequence of major unit operations as the process of the present invention, thus showing only the main products streams and intermediate products.

The present invention describes a process for obtaining lactic acid from the steps of clarification, regeneration, purification and concentration of lactic acid derived from a fermentative liquor containing sodium lactate and several contaminants present in the substrates of the fermentation process.

The proposed process is concerned with energetic efficiency. For this reason, several energetic reuse exchangers were considered and not used for crystallization and washing steps, as proposed in prior art documents.

Another concern of the inventors refers to the use of chemical products that are easily accessible in the marketplace and have reduced cost, contrary to what is stated in previous documents that employ specific solvents.

Lactic acid is produced by fermentation, typically fermentation of a growth medium comprising an sugar solution and a protein, for example, milk protein in the form of permeate milk protein obtained from milk protein concentrate. Fermentation is carried out, preferably by adding one or more protease enzymes to the fermenter, to result in a continuous production of hydrolyzed protein simultaneously with fermentation by means of a bacterial culture that produces lactic acid. Bacterial cultures producing lactic acid are cited, for example, in the international publication WO 98/28433.

This invention conjugates several technologies that can be divided into four steps: clarification, regeneration, purification, and concentration.

The process of the present invention is carried out on a continuous basis. In addition, the process of the present invention further admits batch operation.

The process of the present invention allows obtaining a lactic acid aqueous solution at 80-90% and 0.01 to 3% of impurities.

The process of the present invention combines in a synergistic and successive way the steps described, in order to obtain a concentrated product of high purity with energetic efficiency.

Clarification Step

The load of the process is derived from a fermentative liquor resulting from a dairy fermentation process and consists of an aqueous solution containing 50 to 80 g/L of sodium lactate (more specifically between 60 and 70 g/L), 3 to 5 g/L of cell mass (derived from microorganisms responsible for fermentation process, such as, for example, *Lactobacillus casei*) and fibers (derived from the raw material used in the fermentation, such as, for example, manioc fibers—*Manihot esculenta*), 10 to 50 g/L of polysaccharides (more specifically between 10 g/L and 30 g/L), 1 to 5 g/L of proteins and vitamins and 100 to 500 ppm of bivalent cations ($Mg^{2+}$, $Ca^{2+}$ and $Sr^{2+}$).

The beginning of the process consists of the centrifugation of the fermentative broth, in order to promote the removal of fibers and other suspended solids, thus generating a net stream of pre-clarified fermentative liquor and a wet mud of fibers and cellular material. This operation is essential for the treatment of fermentative liquors that use broths extracted from plants, more specifically of fibrous vegetables.

Practical experience shows that the use of centrifugation upstream other more restrictive filtering operations, such as membranes microfiltration, reduces the frequency of backwash and increases the permeated flow.

The wet mud (containing from 5 to 25% of fermentative liquor) generated in the centrifugation is still impregnated with fermentative liquor, which must be taken out of this pulp, so as to reduce losses of sodium lactate in this clarification step. To achieve this, it is used a centrifugal decanter (decanter) that allows the formation of a dry pulp with 0.5 to 2.5% of residual fermentative liquor. The dry pulp can be sold as a by-product of this process for use in fertilization or as animal feed, to rely on a prior analysis of such viability.

Pre-clarified liquor then passes by a tangential microfiltration through polymeric membranes with pore diameter of 50 μm, preferably 30 μm, which promotes the separation of residual fibers and cells. The stream of liquor held in the microfiltration returns to the entrance of the centrifugation and the microfiltrated liquor stream then passes to the next filtration step.

The microfiltrated liquor feeds the tangential ultrafiltration operation through polymeric membranes with porosity of 30 to 70 kDa, which promotes the separation of macromolecules and cell fragments. The stream of liquor held in the ultrafiltration returns to the entrance of the centrifugation and the ultrafiltrated liquor stream then passes to the next filtration step.

Optionally, the ultrafiltrated liquor stream can be subjected to a nanofiltration step aiming at to reduce the concentration of bivalent cations present in the filtrated medium. Several membranes can be used for this application, such as, for example, polymeric membranes with porosity of 1 to 30 kDa.

The resulting liquor of the ultrafiltration and/or nanofiltration (in case this process is additionally used) feeds the filtration operation in activated carbon bed, which allows for the removal of organic compounds which give color to the aqueous solution. When the load increases considerably in color, one can use powder activated charcoal with 200 rpm shaking and contact time of 10 to 60 minutes prior to bed. As a result, clarified and color-free sodium lactate aqueous solution is obtained.

Regeneration Step

The sodium lactate stream derived from the activated carbon bed proceeds to the step of electrodialysis (EDC), wherein the sodium lactate is purified and concentrated. The EDC consists of applying a potential difference between pairs of positively (anionic membranes) and negatively (cationic membranes) charged membranes. The sodium lactate aqueous solution (50-80 g/L) is fed between a cationic and an anionic membrane (cell) alternately with a diluted solution of 1 to 10 g/L of sodium lactate. This solution receives the lactate anion that migrates by anionic membrane towards the anode and the sodium cation by negatively charged side. At the end of the process, the sodium lactate aqueous solution is exhausted and the non-ionizable polysaccharides, proteins and vitamins remain in this stream, which returns to the step of centrifugation and/or fermentation. The yield of this step varies from 70 to 90% of recovery, depending on the operating conditions (flow, pressure, stream, DDP, pH, concentration, etc.). The sodium lactate diluted solution can be concentrated in up to 20 times with total residual impurities contents of 1 to 10% and 50 to 200 ppm of bivalent cations ($Mg^{2+}$, $Ca^{2+}$ and $Sr^{2+}$).

Sodium lactate is converted to lactic acid by bipolar electrodialysis. The operating principle of bipolar electrodialysis is similar to EDC, except for the addition of a bipolar membrane (positive and negative charges) in each cell (1 cationic membrane and 1 anionic membrane). Bipolar membranes are sensitive to polyvalent cations that settle on the surface of them, thus reducing the efficiency of regeneration. The polyvalent cations are removed from the lactic acid solution for contents of up to 10 ppm in chelating resins filters before the bipolar electrodialysis. At the end of bipolar electrodialysis, it is obtained a solution with concentrations between 80 and 200 g/L of lactic acid, 1 to 5% of total impurities and 10 to 20% sodium lactate. The final polishing for regeneration of all the sodium lactate in lactic acid is performed on a column with strong ionic exchange resins. The regenerated product is then forwarded to the purification step to remove the remaining impurities.

Purification Step

Lactic acid solution with 1 to 5% of impurities is sent to a evaporation column, which will be concentrated in to 60% by mass. The evaporation step concentrates organic compounds which give color to the product, thus requiring a new activated carbon filtration step for complete removal of coloring. This stream of concentrated lactic acid (400 to 600 g/L) and free of color is admitted in a first column of liquid-liquid extraction, where will contact with an average molecular weight alcohol selected amongst linear and/or branched $C_4$-$C_{12}$ alcohols (for example: butanol, pentanol, octanol, decanol, dodecanol, etc.), high molecular weight tertiary amines or a mixture of these alcohols with tertiary amines (e.g.: trioctylamine). The alcoholic stream rich in lactic acid follows to a second column, where it will be rinsed with demineralized water and will return in a closed circuit to the first column. At the end of the cycle, it has an aqueous stream with 5 to 20 g/L of lactic acid and an exhausted stream which is disposed of or reused in the fermentation process. The 5 to 20 g/L colorless lactic acid aqueous solution with 0.01 to 3% of total impurities follows to the concentration step.

Concentration Step

The concentration of purified and regenerated lactic acid aqueous solution is performed on a simple evaporation step with the temperature of the mass between 100 and 150 degrees Celsius and top temperature of 100 degrees Celsius under atmospheric pressure. Colorless lactic acid at 80-90% in water and with concentration of impurities between 0.01 and 3% is obtained at the end of the evaporation.

Another alternative that makes the evaporation step faster is the vacuum application to the evaporation system.

The passage of the final product in charcoal filters "Carbon Block" can be performed for final polishing.

Figures that illustrate the different modalities of the process of the present invention are described. It should be made clear to the skilled in the art, however, that several modifications and variations are possible for these figures within the scope of the present invention.

The attached figures correspond to process flowcharts wherein unit operations are numbered by the hundreds 100 (clarification step), 200 (regeneration step), 300 (purification step), 400 (concentration step) and 500 (fermentation step) with materials streams represented by the numerals 1 to 38. Full lines are used to describe the liquid or solid state streams and dashed lines are used to describe steam flows.

The basic sequence of unit operations, including major streams, is described in FIG. 1. The unit operations correspond to centrifugation (101), centrifugal decanting (102), microfiltration (103), ultrafiltration (104), primary filtration in activated carbon bed (105), conventional electrodialysis (201), ion-exchange columns in chelating resin bed (202), bipolar electrodialysis (203), ion-exchange columns (204), primary vacuum evaporation (302), secondary filtration in activated carbon bed (304), liquid-liquid extraction of the aqueous phase to the organic phase (305), contra-extraction of organic phase to aqueous phase (306) and secondary atmospheric evaporation (402).

The fermentative liquor (1) is centrifuged in (101), generating a supernatant liquid stream called pre-clarified fermentative liquor (5), and a dense stream called wet mud (2), composed of fibers and cellular material.

The wet mud (2) is then dehumidified in the centrifugal decanter (102), generating a stream of dry pulp (3).

The pre-clarified fermentative liquor (5) passes through a microfiltration operation (103), generating a stream of microfiltrated liquor (7), which is fed to the ultrafiltration operation (104), generating a stream of ultrafiltrated liquor (9). The ultrafiltrated liquor (9) then passes through a filtration process in activated carbon bed (105), generating a clarified and color-free sodium lactate aqueous solution (10). Alternatively, the stream of ultrafiltrated liquor (9) is submitted to a stepe of nanofiltration (not represented) with the aim of reducing the concentration of bivalent cations present in the filtrate.

The aqueous solution of sodium lactate (10) is fed to a conventional electrodialysis operation (201), generating a concentrated sodium lactate solution (12). The concentrated sodium lactate solution (12) then passes by a ion exchange operation with chelating resins (202), generating a stabilized concentrated sodium lactate solution (13) free of bivalent cations.

The stabilized concentrated sodium lactate solution (13) feeds a bipolar electrodialysis operation (203), promoting the regeneration of lactic acid and generating a stream of pre-regenerated lactic acid (15). The stream of pre-regenerated lactic acid (15) then passes through an ion exchange operation in strong acid resin bed (204), generating a stream of regenerated lactic acid (16).

The regenerated lactic acid stream (16) is concentrated through an operation of primary vacuum evaporation (302), generating a stream of concentrated regenerated lactic acid stream (19). The concentrated regenerated lactic acid stream (19) then passes through a filtration process in activated carbon bed (304), generating a stream of colorless lactic acid (22). The colorless lactic acid stream (22) goes through a sequence of liquid-liquid extractions, namely in the aqueous phase to the organic phase (305) and then of the aqueous phase to the organic phase (306) through contact with a stream of demineralized water (24), generating a stream of impure lactic acid (23) and a diluted lactic acid solution with high purity degree (28).

The diluted lactic acid solution with high purity degree (28) is concentrated through an evaporation secondary operation (402), generating a stream of concentrated lactic acid with high purity degree (30).

Figure 2:
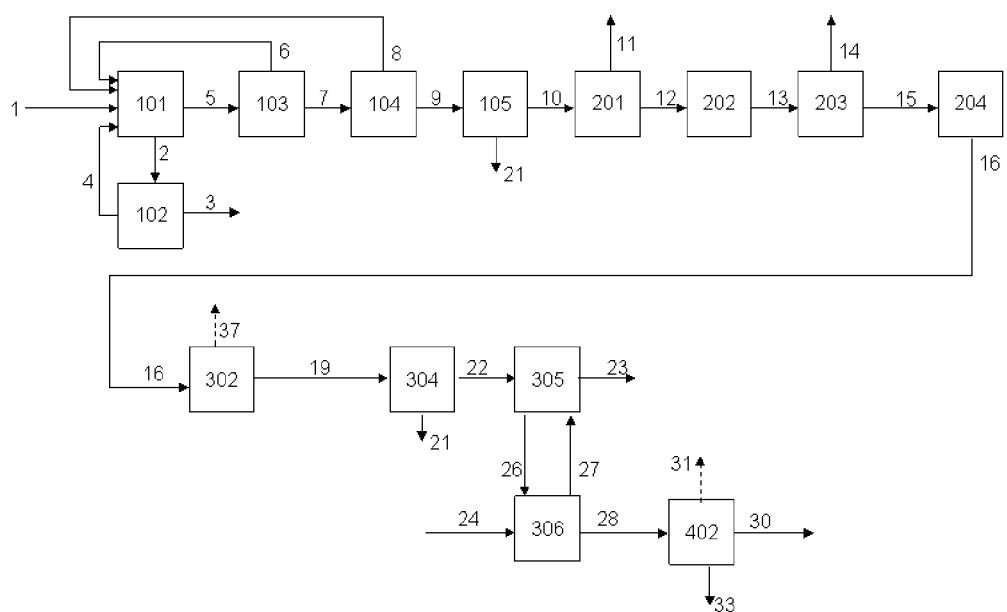
FIG. 2 attached shows a flowchart of the process of the present invention, which describes unit operations and the major streams of the process for producing concentrated lactic acid and with a high purity degree, containing some by-products recycling streams.

FIG. 2 further details the process streams, including by-products, intermediate products and inputs.

The streams of microfiltration concentrate (6), of ultrafiltration concentrate (8) and of centrifugal decanter supernatant (4) are returned to the feeding of centrifugation (101).

The electrodialysis operation (201) generates as a by-product as a stream of diluted sodium lactate (11).

The operation of bipolar electrodialysis (203) generates a stream concentrated of sodium hydroxide (14), which can be used as input to the process.

The operations of evaporation (402 and 302) generate streams of water vapor (37 and 31), which may be used as process utilities.

The operations of filtration in activated carbon medium (105 and 304) generate, intermittently, waste flows (21) during the periods of regeneration of activated carbon bed.

The liquid-liquid extraction operations (305 and 306) have internal recycle streams of organic phase rich in sodium lactate (26) and of the organic phase poor in sodium lactate (27).

The operation of secondary evaporation (402) can generate, depending on the contamination, a stream (33) of precipitated sodium lactate, if the latter is not completely regenerated during the process.

Figure 3:
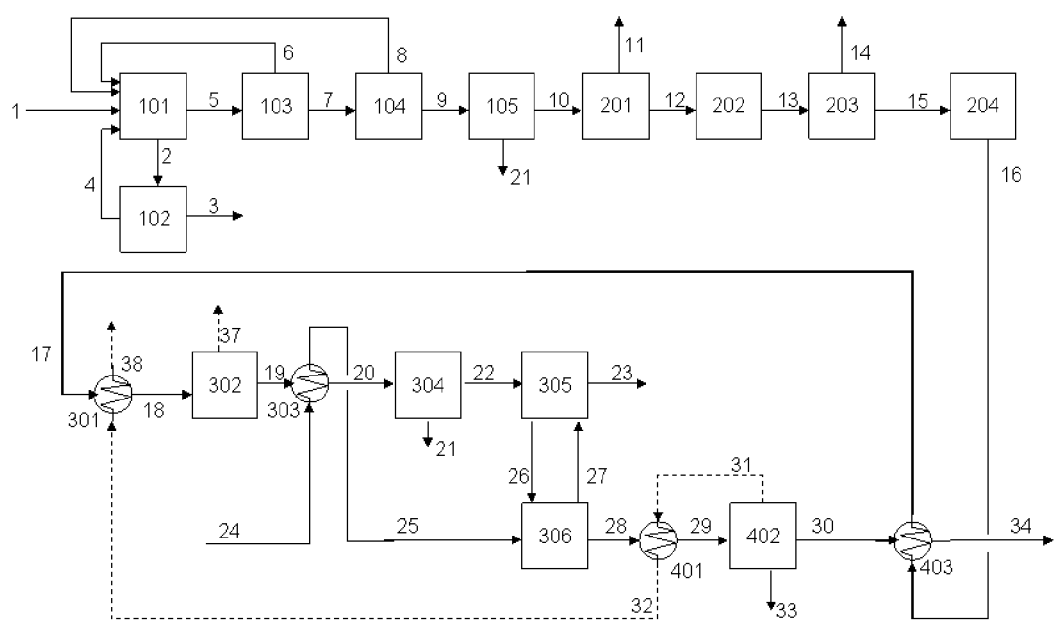
FIG. 3 attached shows a flowchart of the process according to the invention, which illustrates the unit operations and major streams of the process for producing concentrated lactic acid and with a high purity degree, by considering energetic integration.

FIG. 3 incorporates the possibility of energetic reusing by using heat exchangers (301, 303, 401 and 403) for preheating the streams that feed operations (302, 304 and 402). In addition to the energy saving for water evaporation and concentration of streams (16) and (28), heat exchanger (303) allows the stream heating of demineralized water (24), which guarantees an improvement in the performance of the contra-extraction (306).

Figure 4:
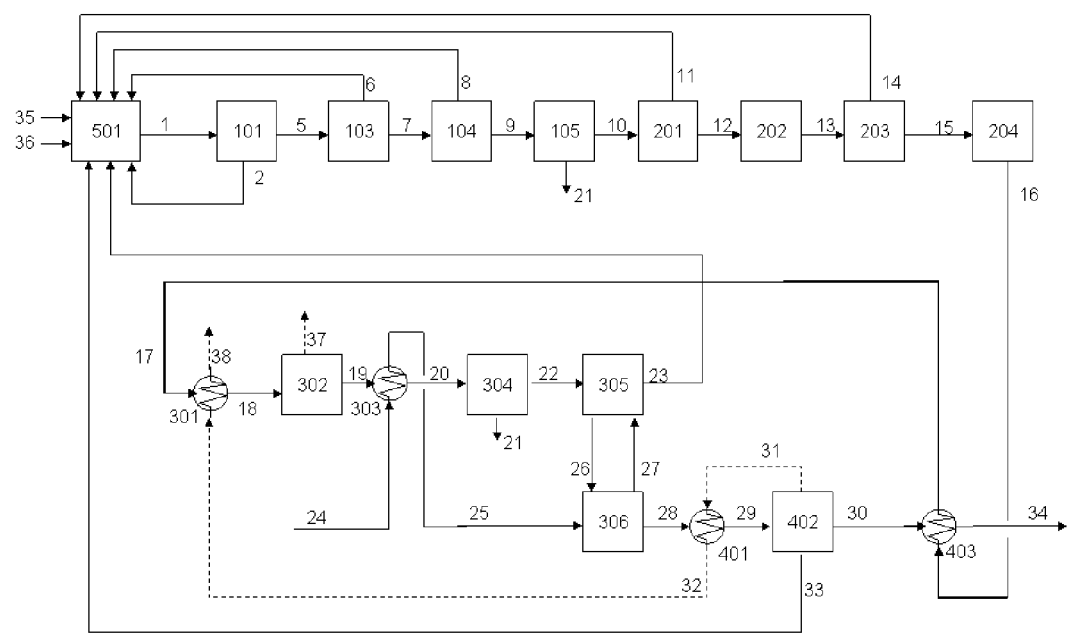
FIG. 4 attached shows a flowchart of the process according to the invention, which illustrates the unit operations and major streams of the process for producing concentrated lactic acid and with a high purity degree by considering energetic integration and mass integration (with by-products recycling streams).

FIG. 4 incorporates the possibility of integrating the process of regeneration, purification and concentration of lactic acid by fermentative process.

Said FIG. 4 includes the operation of fermentation (501), which can be carried out in the form of subsequent or continuously batches.

The stream (35) corresponds to the cells feeding, substrate and other nutrients to the fermentation (501).

The stream (36) corresponds to the caustic soda solution added continuously for the control of fermentation pH (501).

The wet mud stream (2) is recycled to the operation of fermentation (501).

The waste streams of microfiltration and ultrafiltration (6 and 8) are also recycled for operation of fermentation (501).

The stream of lye (11) generated in conventional electrodialysis is also recycled for operation of fermentation (501), in order to promote lactic acid neutralization.

The diluted sodium lactate streams (14) generated as a by-product of bipolar electrodialysis (203), of diluted lactic acid (23) exhausted from the liquid-liquid extraction (305)

and precipitated sodium lactate (33) in the secondary evaporation (402) are recycled to the operation of fermentation (501).

The invention will be illustrated by the following examples, which should not be considered restrictive.

Example 1

This example illustrates the scaling, testing and mass balances for the clarification step.

For a process scaled to treat 250 kg/h of sodium lactate (70 g/L) in a fermentative liquor obtained by fermentation of the milky way, it was considered two distinct scenarios depending on the composition of fermentative liquor. The scenario 1 refers to a liqueur composed of 5 g/L of cells of *Lactobacillus casei* and fibers of *cassava* (*Manihot esculenta*), 5 g/L of vitamins and proteins and 30 g/L of polysaccharides not consumed during the fermentation process. The scenario 2 refers to a liqueur composed of 3 g/L of cells of *Lactobacillus casei* and fibers of *cassava* (*Manihot esculenta*), 1 g/L of vitamins and proteins and 10 g/L of polysaccharides not consumed during the fermentation process.

For the clarification of sodium lactate, a centrifuge capable of a feed of 40 m³/h and 4 m³/h of concentrate, a centrifugal decanter with a capacity of 0.5 m³/h and 0.05 m³/h of concentrate, ultrafiltration and microfiltration systems with processing capabilities of 4 m³/h and 3.5 m³/h of microfiltrated and concentrate, respectively, and a filter in activated carbon bed for filtration of 3.5 m3/h are used.

In relation to the microfiltration system, pilot-scale tests indicated that this system must be operated using timed backwash (at a frequency of 15 to 60 minutes) characterized by pumping in reverse microfiltrated liquor itself. Studies indicated the following optimum project parameters of the microfiltration modules: ratio between the permeate flow and feed flow of about 0.15, permeability of $1.0 \times 10^{-4}$ L/(h·m²·Pa) (10.0 L/(h·m²·bar)) and transmembrane pressure (difference between power and pressures permeate) equal to $1.0 \times 10^5$ Pa (1.0 bar). The membrane area required for this operation is of about 400 m², which corresponds to the use of 8 hollow fiber modules with 50 m² each. The flow rate of the feed pump for this application is 35 m³/h.

In relation to the ultrafiltration system, pilot-scale tests indicated the following optimum project parameters of the ultrafiltration modules: ratio between the permeate flow and feed flow of about 0.50, permeability of $1.5 \times 10^{-4}$ L/(h·m²·Pa) (15.0 L/(h·m²·bar)) and transmembrane pressure (difference between the pressures of power and permeated) of $1.5 \times 10^5$ Pa (1.5 bar). The membrane area required for this operation is of about 150 m², which corresponds to the use of 6 dense flat membrane modules with 25 m² each. The flow rate of the feed pump for this application is of 8 m³/h.

In relation to the activated carbon bed filter, pilot-scale tests indicated the following optimum project parameters: residence time of the solution in contact with the coal equal to 4 hours and a density of coal packaging of about 800 kg/m³. Thus, for the processing of 3.5 m³/h of sodium lactate aqueous solution a vase of 175 L working volume and a coal mass of 140 kg is used. There was also the need for regeneration of coal every 3-6 hours of system operation using steam at 120-150° C.

Pilot-scale tests made it possible to determine mass balances for the clarification step for the two scenarios proposed, considering purging of 25% of the ultrafitration waste (attached Tables 1 and 2) and purging of 10% of the ultrafiltration waste (attached Tables 3 and 4). It is important to stress that as this is a continuous operation and which has the concentration of contaminants by the recycling of ultrafiltration wastes, it becomes necessary to purge part of this stream in order to prevent the elevation of the concentration of this waste within the streams that participate in this recycling.

From attached tables 1 to 4 one can determine the mass yielding of the clarification step in relation to sodium lactate as being equal to about 80% for scenarios 1 and 2, considering a purging of 25% and about 90% for scenarios 1 and 2 considering a purging of 10%.

Example 2

This example illustrates the scaling, testing and mass balances for the concentration step.

For a process scaled without energetic reuse for the concentration of 250 kg/h of sodium lactate sourced from a purified and regenerated lactic acid aqueous solution with lactic acid concentration equal to 15 g/L, it is necessary to use an atmospheric evaporator with heat exchange capacity of about 12 MW for the withdrawal of 16.3 tons/hour of water vapor with a system for the separation of 17 kg/h of insoluble impurities, as described in the attached Table 5 that lists the mass balance of the concentration step. From this table, it is possible to estimate a consumption of about 172 MJ/kg of lactic acid.

On the other hand, a process scale with energetic reuse include a heat exchanger with thermal exchange capacity of about 1.3 MW for preheating the regenerated and purified lactic acid aqueous solution of from 25° C. to 90° C., using hot fluid as the water vapor generated in atmospheric evaporator, as described in the attached Table 6. From this table, it is possible to estimate a consumption of about 153 MJ/kg of lactic acid.

Example 3

This example illustrates the scaling, testing and mass balances for primary evaporation of the purification step.

For a process scaled without energetic reuse for the concentration of 250 kg/h of sodium lactate sourced from a purified and regenerated lactic acid aqueous solution with lactic acid concentration equal to 125 g/L, it is necessary to use a vacuum evaporator ($2.5 \times 10^4$ Pa–250 mbar) with thermal exchange capacity of around 1.0 MW for the withdrawal of 0.6 tons/hour of water vapors, as described in attached Table 7, that lists the primary evaporation mass balance of the purification step. From this table, it is possible to estimate a consumption of about 15.2 MJ/kg of lactic acid.

However, a process scaled with energetic reuse includes a heat exchanger with thermal exchange capacity of about 1.0 MW for pre-heating and evaporation of regenerated diluted lactic acid solution of from 25° C. to 80° C., using hot fluid as water vapor at 120° C. generated in atmospheric evaporator, as described in the attached Table 8.

In this way, it is possible to promote primary evaporation using only the hot fluid generated in the concentration step.

Example 4

This example illustrates the scaling, testing and mass balances for the liquid-liquid extraction of the purification step.

For a process scaled for the purification of 250 kg/h of lactic acid sourced from a concentrated lactic acid aqueous solution (500 g/L) a conventional first column of liquid-liquid extraction to contact 500 L/h of concentrated lactic acid solution with 1.0 m3/h of octanol and a second column of liquid-liquid contra-extraction to contact 1.0 m³/h of octanol with 1.0 m³/h of demineralized water are used. As a result, it is retrieved an aqueous stream with a flow of 1.0 m³/h of purified lactic acid diluted solution at a concentration of 15 µg/l.

The water streams enter into the lower part of the extractor columns and the alcoholic streams at the top, for the octanol density (0.8 g/mL) is less than that of water (1.0 µg/mL).

The first conventional column has 20 theoretical plates with 1.5 meters in diameter and has a decanter in the output of alcoholic phase to aqueous solution drag retention. The octanol derived from the first column is under pressure and overflows from the decanter to the bottom of the second column.

The second conventional column has the same characteristics as the first and the octanol exhausted from the decanter is recovered in the first column, remaining thus in a closed circuit.

Pilot-scale tests have provided a 70% recovery of lactic acid in the first passage through the system. It is worth noting that the remaining 30% lactic acid can be further concentrated in the evaporation system and resubmitted for new liquid-liquid extraction, resulting in losses to the process.

Example 5

This example illustrates the scaling, testing and mass balances for the conventional electrodialysis step of regeneration.

For a process scaled for the concentration of 250 kg/h of sodium lactate from a diluted solution of 70 g/L of sodium lactate a module (stack) of conventional electrodialysis (EDC) with capacity for 3.6 m³/h is used. Considering a stream density of 110 A/m² with stream efficiency of 80% and a 155 V voltage, it is required a 175 m² membrane area.

This process has a yield of about 80%, from 6.5 m³/h of a solution of 5 g/L sodium lactate, and generates as a by-product 6.5 m³/h of a sodium lactate-poor aqueous solution (14 g/L) containing polysaccharides, proteins and vitamins. The electrolytes consume 3 m³/h of a solution of sulfuric acid at 2%. The product corresponds to a flow rate of 3.5 m³/h of lactic acid solution with a concentration of 125 g/L.

Example 6

This example illustrates the scaling, testing and mass balances for the bipolar electrodialysis of the regeneration step.

For a process scaled for the regeneration of 200 kg/h of sodium lactate from a 125 g/L of sodium lactate solution a module (stack) of bipolar electrodialysis (EDBM) with a capacity of 3.0 m³/h treatment is used. Considering a stream density of 600 A/m² with stream efficiency of 70%, a stream average of 2.5 and a 165 V voltage, a 85 m² membrane area is required.

This process presents a yield of about 90% of lactic acid in relation to the sodium lactate fed. The product corresponds to a flow rate of 3.0 m³/h of lactic acid solution with concentration of 112.5 g/L of lactic acid and 12.5 g/L of sodium lactate.

It should be made clear to the skilled in the art that although the present invention has been described in relation to lactic acid, many other carboxylic acids can also undergo a similar process, such acids including: formic acid, acetic acid, butyric acid, propionic acid, valeric acid, isovaleric acid, capronic acid, acid heptanoic acid, octanic acid, oxalic acid, maloic acid, glutaric acid, adipic acid, glycolic acid, glycinic acid, acrylic acid, tartaric acid, fumaric acid, benzoic acid, maleic acid, phthalic acid or salicylic acid.

TABLE 1

Mass balance of the clarification step for scenario 1 with purging of 25% of the ultrafiltration waste

|  | Fermentative liquor | Wet mud (centrifugation decantated) | Dry pulp (cells and fibers) | Centrifugal decanter supernatant | Pre-clarified liquor (centrif. supernatant) | Microfiltration waste | Microfiltrated liquor | Ultrafiltration waste | Ultrafiltrated liquor | Sodium lactate aqueous solution | Ultrafiltration waste purging |
|---|---|---|---|---|---|---|---|---|---|---|---|
| Indexes | 1 | 2 | 3 | 4 | 5 | 6 | 7 | 8 | 9 | 10 |  |
| Volumetric flow (L/h) | 3571 | 179 | 24 | 155 | 37968 | 32273 | 5695 | 2848 | 2848 | 2148 | 700 |
| Concentration (g/L) |  |  |  |  |  |  |  |  |  |  |  |
| Fibers and Cells | 5.0 | 200.0 | 750.0 | 115.4 | 10.5 | 12.4 | 0.0 | 0.0 | 0.0 | 0.0 | 0.0 |
| Sodium lactate | 70.0 | 70.2 | 70.2 | 70.2 | 70.2 | 70.2 | 70.2 | 70.2 | 70.2 | 70.2 | 70.2 |
| Bivalent cations | 0.5 | 0.5 | 0.5 | 0.5 | 0.5 | 0.5 | 0.5 | 0.5 | 0.5 | 0.5 | 0.5 |
| Proteins and vitamins | 5.0 | 10.0 | 10.0 | 10.0 | 10.0 | 10.0 | 10.0 | 20.0 | 0.0 | 0.0 | 20.0 |
| Polysaccharides | 30.0 | 30.0 | 30.0 | 30.0 | 30.0 | 30.0 | 30.0 | 30.0 | 30.0 | 25.0 | 30.0 |
| Mass flow (kg/h) |  |  |  |  |  |  |  |  |  |  |  |
| Fibers and Cells | 18 | 36 | 18 | 18 | 399 | 399 | 0 | 0 | 0 | 0 | 0 |
| Sodium lactate | 250 | 13 | 2 | 11 | 2667 | 2267 | 400 | 200 | 200 | 151 | 49 |
| Bivalent cations | 2 | 0 | 0 | 0 | 19 | 16 | 3 | 1 | 1 | 1 | 0 |
| Proteins and vitamins | 18 | 2 | 0 | 2 | 380 | 323 | 57 | 57 | 0 | 0 | 14 |
| Polysaccharides | 107 | 5 | 1 | 5 | 1140 | 969 | 171 | 85 | 85 | 54 | 21 |

TABLE 2

Mass balance of the clarification step for scenario 2 with purging of 25% of the ultrafiltration waste

|  | Fermentative liquor | Wet mud (centrifugation decantated) | Dry pulp (cells and fibers) | Centrifugal decanter supernatant | Pre-clarified liquor (centrif. supernatant) | Microfiltration waste | Microfiltrated liquor | Ultrafiltration waste | Ultrafiltrated liquor | Sodium lactate aqueous solution | Ultrafiltration waste purging |
|---|---|---|---|---|---|---|---|---|---|---|---|
| Indexes | 1 | 2 | 3 | 4 | 5 | 6 | 7 | 8 | 9 | 10 |  |
| Volumetric flow (L/h) | 3571 | 179 | 14 | 164 | 38095 | 32381 | 5714 | 2857 | 2857 | 2157 | 700 |
| Concentration (g/L) |  |  |  |  |  |  |  |  |  |  |  |
| Fibers and Cells | 3.0 | 200.0 | 750.0 | 152.2 | 10.5 | 12.4 | 0.0 | 0.0 | 0.0 | 0.0 | 0.0 |
| Sodium lactate | 70.0 | 70.2 | 70.2 | 70.2 | 70.2 | 70.2 | 70.2 | 70.2 | 70.2 | 70.2 | 70.2 |
| Bivalent cations | 0.5 | 0.5 | 0.5 | 0.5 | 0.5 | 0.5 | 0.5 | 0.5 | 0.5 | 0.5 | 0.5 |
| Proteins and vitamins | 1.0 | 2.0 | 2.0 | 2.0 | 2.0 | 2.0 | 2.0 | 4.0 | 0.0 | 0.0 | 4.0 |
| Polysaccharides | 10.0 | 10.0 | 10.0 | 10.0 | 10.0 | 10.0 | 10.0 | 10.0 | 10.0 | 25.0 | 10.0 |
| Mass flow (kg/h) |  |  |  |  |  |  |  |  |  |  |  |
| Fibers and Cells | 11 | 36 | 11 | 25 | 401 | 401 | 0 | 0 | 0 | 0 | 0 |
| Sodium lactate | 250 | 13 | 1 | 12 | 2675 | 2274 | 401 | 201 | 201 | 151 | 49 |
| Bivalent cations | 2 | 0 | 0 | 0 | 19 | 16 | 3 | 1 | 1 | 1 | 0 |
| Proteins and vitamins | 4 | 0 | 0 | 0 | 76 | 65 | 11 | 11 | 0 | 0 | 3 |
| Polysaccharides | 36 | 2 | 0 | 2 | 381 | 324 | 57 | 29 | 29 | 54 | 7 |

TABLE 3

Mass balance of the clarification step for scenario 1 with purging of 10% of the ultrafiltration waste

|  | Fermentative liquor | Wet mud (centrifugation decantated) | Dry pulp (cells and fibers) | Centrifugal decanter supernatant | Pre-clarified liquor (centrif. supernatant) | Microfiltration waste | Microfiltrated liquor | Ultrafiltration waste | Ultrafiltrated liquor | Sodium lactate aqueous solution | Ultrafiltration waste purging |
|---|---|---|---|---|---|---|---|---|---|---|---|
| Indexes | 1 | 2 | 3 | 4 | 5 | 6 | 7 | 8 | 9 | 10 |  |
| Volumetric flow (L/h) | 3571 | 179 | 24 | 155 | 43302 | 36806 | 6495 | 3248 | 3248 | 2948 | 300 |
| Concentration (g/L) |  |  |  |  |  |  |  |  |  |  |  |
| Fibers and Cells | 5.0 | 200.0 | 750.0 | 115.4 | 10.6 | 12.5 | 0.0 | 0.0 | 0.0 | 0.0 | 0.0 |
| Sodium lactate | 70.0 | 70.2 | 70.2 | 70.2 | 70.2 | 70.2 | 70.2 | 70.2 | 70.2 | 70.2 | 70.2 |
| Bivalent cátions | 0.5 | 0.5 | 0.5 | 0.5 | 0.5 | 0.5 | 0.5 | 0.5 | 0.5 | 0.5 | 0.5 |
| Proteins and vitamins | 5.0 | 25.0 | 25.0 | 25.0 | 25.0 | 25.0 | 25.0 | 50.0 | 0.0 | 0.0 | 50.0 |
| Polysaccharides | 30.0 | 30.0 | 30.0 | 30.0 | 30.0 | 30.0 | 30.0 | 30.0 | 30.0 | 25.0 | 30.0 |
| Mass flow (kg/h) |  |  |  |  |  |  |  |  |  |  |  |
| Fibers and Cells | 18 | 36 | 18 | 18 | 460 | 460 | 0 | 0 | 0 | 0 | 0 |
| Sodium lactate | 250 | 13 | 2 | 11 | 3041 | 2585 | 456 | 228 | 228 | 207 | 21 |
| Bivalent cátions | 2 | 0 | 0 | 0 | 22 | 18 | 3 | 2 | 2 | 1 | 0 |
| Proteins and vitamins | 18 | 4 | 1 | 4 | 1083 | 921 | 162 | 162 | 0 | 0 | 15 |
| Polysaccharides | 107 | 5 | 1 | 5 | 1300 | 1105 | 195 | 97 | 97 | 74 | 9 |

TABLE 4

Mass balance of the clarification step for scenario 2 with purging of 10% of the ultrafiltration waste

|  | Fermentative liquor | Wet mud (centrifugation decantated) | Dry pulp (cells and fibers) | Centrifugal decanter supernatant | Pre-clarified liquor (centrif. supernatant) | Microfiltration waste | Microfiltrated liquor | Ultrafiltration waste | Ultrafiltrated liquor | Sodium lactate aqueous solution | Ultrafiltration waste purging |
|---|---|---|---|---|---|---|---|---|---|---|---|
| Indexes | 1 | 2 | 3 | 4 | 5 | 6 | 7 | 8 | 9 | 10 |  |
| Volumetric flow (L/h) | 3571 | 179 | 14 | 164 | 72381 | 61524 | 10857 | 7600 | 3257 | 2957 | 300 |
| Concentration (g/L) |  |  |  |  |  |  |  |  |  |  |  |
| Fibers and Cells | 3.0 | 200.0 | 750.0 | 152.2 | 10.9 | 12.9 | 0.0 | 0.0 | 0.0 | 0.0 | 0.0 |
| Sodium lactate | 70.0 | 70.2 | 70.2 | 70.2 | 70.2 | 70.2 | 70.2 | 70.2 | 70.2 | 70.2 | 70.2 |
| Bivalent cations | 0.5 | 0.5 | 0.5 | 0.5 | 0.5 | 0.5 | 0.5 | 0.5 | 0.5 | 0.5 | 0.5 |

TABLE 4-continued

Mass balance of the clarification step for scenario 2 with purging of 10% of the ultrafiltration waste

|  | Fermentative liquor | Wet mud (centrifugation decanted) | Dry pulp (cells and fibers) | Centrifugal decanter supernatant | Pre-clarified liquor (centrif. supernatant) | Microfiltration waste | Microfiltrated liquor | Ultrafiltration waste | Ultrafiltrated liquor | Sodium lactate aqueous solution | Ultrafiltration waste purging |
|---|---|---|---|---|---|---|---|---|---|---|---|
| Proteins and vitamins | 1.0 | 4.0 | 4.0 | 4.0 | 4.0 | 4.0 | 4.0 | 5.7 | 0.0 | 0.0 | 5.7 |
| Polysaccharides | 10.0 | 10.0 | 10.0 | 10.0 | 10.0 | 10.0 | 10.0 | 10.0 | 10.0 | 25.0 | 10.0 |
| Mass flow (kg/h) | | | | | | | | | | | |
| Fibers and Cells | 11 | 36 | 11 | 25 | 791 | 791 | 0 | 0 | 0 | 0 | 0 |
| Sodium lactate | 250 | 13 | 1 | 12 | 5082 | 4320 | 762 | 534 | 229 | 208 | 21 |
| Bivalent cations | 2 | 0 | 0 | 0 | 36 | 31 | 5 | 4 | 2 | 1 | 0 |
| Proteins and vitamins | 4 | 1 | 0 | 1 | 290 | 246 | 43 | 43 | 0 | 0 | 2 |
| Polysaccharides | 36 | 2 | 0 | 2 | 724 | 615 | 109 | 76 | 33 | 74 | 3 |

TABLE 5

|  | Pure diluted lactic acid solution | Pure concentrated lactic acid solution | Water vapor | Precipitated sodium lactate |
|---|---|---|---|---|
| Indexes | 28 | 30 | 31 | 32 |
| Temperature (° C.) | 25 | 120 | 120 | 120 |
| Mass flow (kg/h) | 12500 | 333 | 12165 | 1 |
| Volumetric flow (L/h) | 12500 | 278 | — | 1 |
| Concentration (g/L) | | | | |
| Sodium lactate and Impurities | 0.1 | 0.0 | 0.0 | 1000.0 |
| Lactic acid | 20.0 | 900.0 | 0.0 | 20.0 |
| Mass flow (kg/h) | | | | |
| Sodium lactate and Impurities | 1.3 | 0 | 0 | 1.3 |
| Lactic acid | 250 | 250 | 0 | 0.0 |

TABLE 7

|  | Regenerated diluted lactic acid solution | Regenerated lactic acid concentrated solution | Water vapor |
|---|---|---|---|
| Indexes | 16 | 19 | 37 |
| Temperature (° C.) | 25 | 80 | 80 |
| Mass flow (kg/h) | 2000 | 600 | 1400 |
| Volumetric flow (L/h) | 2000 | 500 | — |
| Concentration (g/L) | | | |
| Sodium lactate and Impurities | 25 | 100.0 | 0.0 |
| Lactic acid | 125.0 | 500.0 | 0.0 |
| Mass flow (kg/h) | | | |
| Sodium lactate and Impurities | 50 | 50 | 0 |
| Lactic acid | 250 | 250 | 0 |

TABLE 6

|  | Pure diluted lactic acid solution | Pre-heated diluted lactic acid solution | Pure concentrated lactic acid solution | Water vapor | Water vapor post energetic reuse | Precipitated sodium lactate |
|---|---|---|---|---|---|---|
| Indexes | 28 | 29 | 30 | 31 | 31 | 32 |
| Temperature (° C.) | 25 | 90 | 120 | 120 | 100 | 120 |
| Mass flow (kg/h) | 16666 | 16666 | 333 | 16316 | 16316 | 17 |
| Volumetric flow (L/h) | 16666 | 16666 | 277 | — | — | 14 |
| Concentration (g/L) | | | | | | |
| Sodium lactate and Impurities | 1.0 | 1.0 | 0.0 | 0.0 | 0.0 | 1000.0 |
| Lactic acid | 15.0 | 15.0 | 900.0 | 0.0 | 0.0 | 20.0 |
| Mass flow (kg/h) | | | | | | |
| Sodium lactate and Impurities | 16.7 | 16.7 | 0 | 0 | 0 | 16.7 |
| Lactic acid | 250 | 250 | 250 | 0 | 0 | 0.3 |

TABLE 8

|  | Regenerated diluted lactic acid solution | Pre-heated regenerated diluted lactic acid solution | Regenerated lactic acid concentrated solution | Water vapor | water vapor before energetic reuse | Condensed after energetic reuse |
|---|---|---|---|---|---|---|
| Indexes | 17 | 18 | 19 | 37 | 32 | 38 |
| Temperatura (° C.) | 25 | 80 | 80 | 80 | 100 | 100 |
| Mass flow (kg/h) | 2000 | 2000 | 600 | 1400 | 1603 | 1603 |
| Volumetric flow (L/h) | 2000 | 2000 | 500 | — | — | — |
| Concentration (g/L) | | | | | | |
| Sodium lactate and Impurities | 25.0 | 25.0 | 100.0 | 0.0 | 0.0 | 0.0 |
| Ácido Lático | 125.0 | 125.0 | 500.0 | 0.0 | 0.0 | 0.0 |
| Mass flow (kg/h) | | | | | | |
| Sodium lactate and Impurities | 50.0 | 50 | 50 | 0 | 0 | 0.0 |
| Ácido Lático | 250 | 250 | 250 | 0 | 0 | 0.0 |

The invention claimed is:

1. A process for obtaining lactic acid with high purity degree from fermentative liquor containing sodium lactate, vegetable fibers and polysaccharides, comprising the steps of:
   a) clarification, comprising the following sub-steps:
      a1) centrifuging a fermentative liquor (1), generating a supernatant stream of pre-clarified fermentative liquor (5) and a dense stream of wet mud (2) composed of fibers and cell material containing from 5 to 25% of fermentative liquor, dehumidifying said wet mud (2) in a centrifugal decanter (102), generating a stream of dry pulp (3) with 0.5 to 2.5% residual fermentative liquor;
      a2) microfiltering by tangential microfiltration in (103) the pre-clarified fermentative liquor (5) of substep a1), generating a stream of microfiltrated liquor (7);
      a3) feeding the stream (7) of substep a2) to a tangential ultrafiltration operation (104), generating a stream of ultrafiltrated liquor (9);
      a4) filtering in activated carbon bed (105) the ultrafiltrated liquor (9) of substep a3), generating a clarified and colorless sodium lactate aqueous solution (10);
   b) regeneration, comprising the following sub-steps:
      b1) feeding said sodium lactate aqueous solution (10) of substep a4) to a conventional electrodialysis operation (201), generating a sodium lactate concentrated solution (12);
      b2) submitting said solution (12) of substep b1) to ion exchange with chelating resins (202), generating a stabilized sodium lactate concentrated solution (13) free of bivalent cations;
      b3) feeding said solution (13) of substep b2) to a bipolar electrodialysis operation (203), promoting the regeneration of lactic acid and generating a stream of pre-regenerated lactic acid (15) with a concentration of 80-200 g/L of lactic acid and 10-20% of sodium lactate;
      b4) submitting said stream (15) of substep b3) to a bed of strong acid ion-exchange resin operation (204), generating a stream of regenerated lactic acid (16);
   c) purification, comprising the following sub-steps:
      c1) focusing said stream (16) of substep b4) by primary vacuum evaporation (302), generating a stream of concentrated regenerated lactic acid with 1-5% of impurities (19);
      c2) filtering, in a bed of activated carbon (304), said stream (19) of substep c1), generating a stream of colorless lactic acid (22) with 0.1 to 3% of impurities;
      c3) submitting said stream (22) of substep c2) to a liquid-liquid extractions sequence, the first extraction being from the aqueous phase to the organic phase (305), and the second extraction being from the organic phase to the aqueous phase (306) through contact with a demineralized water stream (24) generating, respectively, a stream of impure lactic acid (23) and a lactic acid diluted solution of with high purity degree (28); and
   d) concentration, comprising concentrating the lactic acid diluted solution with high purity degree (28) of substep c3) by secondary evaporation in (402), generating a stream (30) of lactic acid with high purity degree and in the concentration of 80-90%.

2. Process, according to claim 1, characterized in that it returns to the centrifugation feed (101) the concentrated streams of microfiltration (6), the concentrated ultrafiltration (8) and the supernatant (4) of the centrifugal decanter (102).

3. Process, according to claim 1, characterized by additionally performing an operation of nanofiltration in membranes between the substeps a3) and a4).

4. Process, according to claim 1, characterized in that the electrodialysis operation (201) generates as a by-product a stream of diluted sodium lactate (11).

5. Process, according to claim 1, characterized in that the operation of bipolar electrodialysis (203) generates as a by-product a concentrated stream of sodium hydroxide (14).

6. Process, according to claim 5, characterized in that said concentrated stream of sodium hydroxide (14) can be used as input to the process.

7. Process, according to claim 1, characterized in that the filtering operations in the activated carbon medium (105, 304) generate intermittently waste flows (21) during the periods of regeneration of activated carbon bed.

8. Process, according to claim 1, characterized in that in the substep c3) the liquid-liquid extraction is employed a moderate molecular weight alcohol selected among alcohol between C4 and C12, a high molecular weight tertiary amine or a mixture in any proportion of C4-C12 alcohol and said amine.

9. Process, according to claim 8, characterized in that the tertiary amine is the trioctylamine.

10. Process, according to claim 8, characterized in that the C4-C12 alcohol is selected from the group comprised of butanol, pentanol, octanol, decanol, dodecanol or similar.

11. Process, according to claim 1, characterized in that the streams of water vapor (31, 37) generated, respectively, by evaporation (302, 402) are used as process utilities.

12. Process, according to claim 1, characterized in that the liquid-liquid extraction operations (305, 306) generate internal recycle streams of an organic phase rich in sodium lactate (26) and an organic phase poor in sodium lactate (27).

13. Process, according to claim 1, characterized in that the operation of secondary evaporation (402) can generate a precipitated sodium lactate stream (33).

14. Process, according to claim 1, characterized by being effected under energetic reuse through the use of heat exchangers (301, 303, 401 and 403) used for preheating streams that feed operations (302, 304, 402).

15. Process, according to claim 14, characterized in that the heat exchanger (303) heats the water stream (24) for the operation of counter-extraction (306).

16. Process, according to claim 1, characterized by further including the operation of batch fermentation (501), a power stream (35) and a stream of sodium hydroxide (36) being added to the fermenter.

17. Process, according to claim 1, characterized by further including the operation of continuous fermentation (501), being added to the fermenter a power stream (35) and a stream of sodium hydroxide (36).

18. Process, according to claim 16, characterized in that the power supply stream (35) consists of a fermentation broth by milk fermenting containing 50 to 80 g/L of sodium lactate, 3 to 5 g/L of cells and fibers, 10 to 50 g/L of polysaccharides, 1 to 5 g/L of protein and vitamins and 100 to 500 ppm of bivalent cations.

19. Process, according to claim 18, characterized in that the concentration of sodium lactate is preferably from 60 to 70 g/L.

20. Process, according to claim 18, characterized in that the concentration of polysaccharides is preferably 10 to 30 g/L.

21. Process, according to claim 1, characterized in that the wet mud stream (2), the waste streams of microfiltration (6) and ultrafiltration (8), the stream of lye (11) generated in conventional electrodialysis, the stream of diluted sodium lactate (14) generated as a by-product of bipolar electrodialysis (203), the stream of dilute lactic acid (23) exhausted from liquid-liquid extraction (305) and stream of sodium lactate precipitate (33) in the secondary evaporation (402) are recycled to the operation of fermentation (501).

* * * * *